US00PP16776P2

(12) United States Plant Patent
Kobayashi

(10) Patent No.: US PP16,776 P2
(45) Date of Patent: Jul. 11, 2006

(54) POINSETTIA PLANT NAMED 'PER10101'

(50) Latin Name: *Euphorbia pulcherrima*
Varietal Denomination: PER10101

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 58 days.

(21) Appl. No.: 10/955,488

(22) Filed: Sep. 30, 2004

(51) Int. Cl.
*A01H 5/00* (2006.01)

(52) U.S. Cl. ..... Plt./303

(58) Field of Classification Search ..... Plt./303
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Poinsettia plant named 'PER10101', characterized by its inflorescences with pale yellow and pale pink bi-colored flower bracts; dark green-colored leaves; uniform, compact, upright and mounded plant habit; early season flowering; nature season flower maturity date is late November for planta grown in Encinitas, Calif.; and excellent post-production longevity.

1 Drawing Sheet

Botanical classification/cultivar designation: *Euphorbia pulcherrima* Willd. cultivar PER10101.

BACKGROUND OF THE INVENTION

The present Invention relates to a new and distinct cultivar of Poinsettia plant, botanically known as *Euphorbia pulcherrima* Willd., and hereinafter referred to by the name 'PER10101'.

The new Poinsettia a product of a planned breeding program conducted by the Inventor in Encinitas, Calif. The objective of the breeding program is to create new early flowering Poinsettia cultivars having strong stems, attractive flower bract coloration, uniform plant habit and excellent post-production longevity.

The new Poinsettia is a naturally-occurring whole mutation of the Poinsettia cultivar Eckakmal, disclosed in U.S. Plant Pat. No. 13,827. The new Poinsettia was discovered and selected by the Inventor in a controlled environment in Encinitas, Calif. on Mar. 29, 2001. The new Poinsettia was selected on the basis its unique flower bract coloration.

Asexual reproduction of the new Poinsettia by terminal cuttings propagated in a conrolled environment in Encinitas, Calif., since February, 2003, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'PER10101'. These characteristics in combination distinguish 'PER10101' as a new and distinct cultivar:

1. Inflorescences with pale yellow and pale pink bi-colored flower bracts.
2. Dark green-colored leaves.
3. Uniform, compact, upright and mounded plant habit.
4. Early season flowering; natural season flower maturity date is mid-November for plants grown in Encinitas, Calif.
5. Excellent post-production longevity.

Plants of the new Poinsettia are most similar to plants of the parent, the cultivar Eckakmal. Plants of the new Poinsettia differ from plants of the cultivar Eckakmal primarily in flower bract color as plants of the cultivar Eckakmal have solid pink-colored flower bracts.

Plants of the new Poinsettia can be compared to plants of the cultivar Eckadria, disclosed in U.S. Plant Pat. No. 12,725. In side-by-side comparisons conducted in Encinitas, Calif., plants of the new Poinsettia differed primarily from plants of the cultivar Eckadria in flower bract coloration as plants of the cultivar Eckadria had red-colored flower bracts with random pink-colored flecks.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the top of the sheet comprises a side perspective view of a typical flowering plant of 'PER10101' grown in a container.

The photograph at the bottom of the sheet comprises a top perspective view of a typical plant of 'PER10101'.

DETAILED BOTANICAL DESCRIPTION

The new Poinsettia has not been observed under all possible environmental conditions, The phenotype may vary somewhat with variations in environment such as temperature, daylength and light intensity, without, however, any variance in genotype.

The aforementioned photographs, following observations and averaged measurements describe plants grown in Encinitas, Calif. during the autumn under commercial practice in a polycarbonate-covered greenhouse with day temperatures averaging about 29° C., night temperatures averaging about 19° C. and light levels about 4,000 foot-candles. Single plants were grown in 16.5 -cm pots and pinched once.

Plants were flowered under natural season short day/long night confitions. Plants were about 17 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar PER10101.

Parentage: Naturally-occurring branch mutation of the Poinsettia cultivar Eckakmal, disclosed in U.S. Plant Pat. No. 13,827.

Propagation:

*Type cutting.*—Terminal cuttings.

*Time to initiate roots.*—About 10 days at 20 to 22° C.

*Time to develop roots.*—About 28 days at 20 to 22° C.

*Root description.*—Thick, fibrous, freely-branching; white in color.

Plant description:

*Plant form.*—Inverted triangle; top of plant mounded.

*Growth habit.*—Upright, compact and uniform plant habit. Moderately vigorous to vigorous.

*Plant height.*—About 30 cm.

*Plant diameter or spread.*—About 43 cm.

*Lateral branch description.*—Quantity: About ten lateral branches develop after pinching. Length: About 23 cm. Diameter: About 6 mm. Internode length: About 2 to 2.5 cm. Strength: Strong. Texture: Smooth; glabrous. Color: 144A.

*Foliage description.*—Arrangement: Alternate, single. Length: About 15 cm. Width: About 12 cm. Shape: Ovate with irregular shallow lobing. Apex: Acuminate. Base: Acute to obtuse. Margin: Entire with irregular shallow lobing. Venation pattern: Pinnate. Texture, upper surface: Glabrous, smooth. Texture, lower surface: Slightly pubescent. Surface: Rugose. Aspect: Flat; recurving slightly with development. Color: Developing and fully expanded foliage, upper surface: Darker than 147A. Developing and fully expanded foliage, lower surface: 137B. Venation, upper surface: 144C to 144D. Venation, lower surface: 145B. Petiole: Length: About 1.5 cm. Diameter: About 3 mm. Texture, upper and lower surfaces: Smooth; glabrous. Color: 144B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent.

*Natural flowering season.*—Autumn/winter in Northern Hemisphere. Flower initiation and development is induced under long nyctoperiod conditions. Early season flowering, response time, about 8 weeks; natural season flower maturity date is late November for plants grown in Encinitas, Calif.

*Post-production longevity.*—Plants of the new Poinsettia maintain good substance and bract color for about four weeks under interior conditions.

*Inflorescence size.*—Diameter: About 26 cm. Height (depth): About 3 to 3.5 cm.

*Flower bracts.*—Quantity per inflorescence: About 21. Length, largest bracts: About 15 cm. Width, largest bracts: About 8 cm. Shape: Ovate to elliptic with irregular shallow lobing. Apex: Acuminate. Base: Acute. Margin: Entire with irregular shallow lobing. Texture, upper and lower surfaces: Glabrous; velvety. Surface: Slightly rugose. Aspect: Flat to slightly recurved with development. Venation pattern: Pinnate. Color: Developing or transitional bracts, upper and lower surfaces: Center, 47C; surrounding the center and towards the margins, 8B. Fully developed bracts, upper and lower surfaces: Center, 49A to 49B; surrounding the center and towards the margins, 10C; center area becoming closer to 49C to 49D with development. Venation, upper and lower surfaces: Similar to flower bract color. Bract petiole: Length: About 1 cm. Diameter: About 2 mm. Texture, upper and lower surfaces: Smooth; glabrous. Color: 144A.

*Cyathia.*—Quantity per corymb: About 16. Diameter of cyathia cluster: About 3.5 cm. Length: About 1 cm. Width: About 5 mm. Shape: Ovoid. Color, immature and mature: 144A. Peduncle: Length: About 3 mm. Diameter: About 2.5 mm. Strength: Strong. Aspect: Mostly upright to outward. Texture: Smooth; glabrous. Color: 144B. Stamens: Quantity per cyathium: About 20. Anther shape: Oval. Anther length: Less than 1 mm. Anther color: 19B. Amount of pollen: Scarce. Pollen color: 10A. Pistils: None observed. Nectaries: Quantity per cyathium: About one or two. Size: About 3 mm by 5 mm. Color: 14A.

Disease/pest resistance: Resistance to pathogens and pests common to Poinsettias has not been observed on planta grown under commercial conditions.

It is claimed:

1. A new and distinct cultivar of Poinsettia plant named 'PER10101', as illustrated and described.

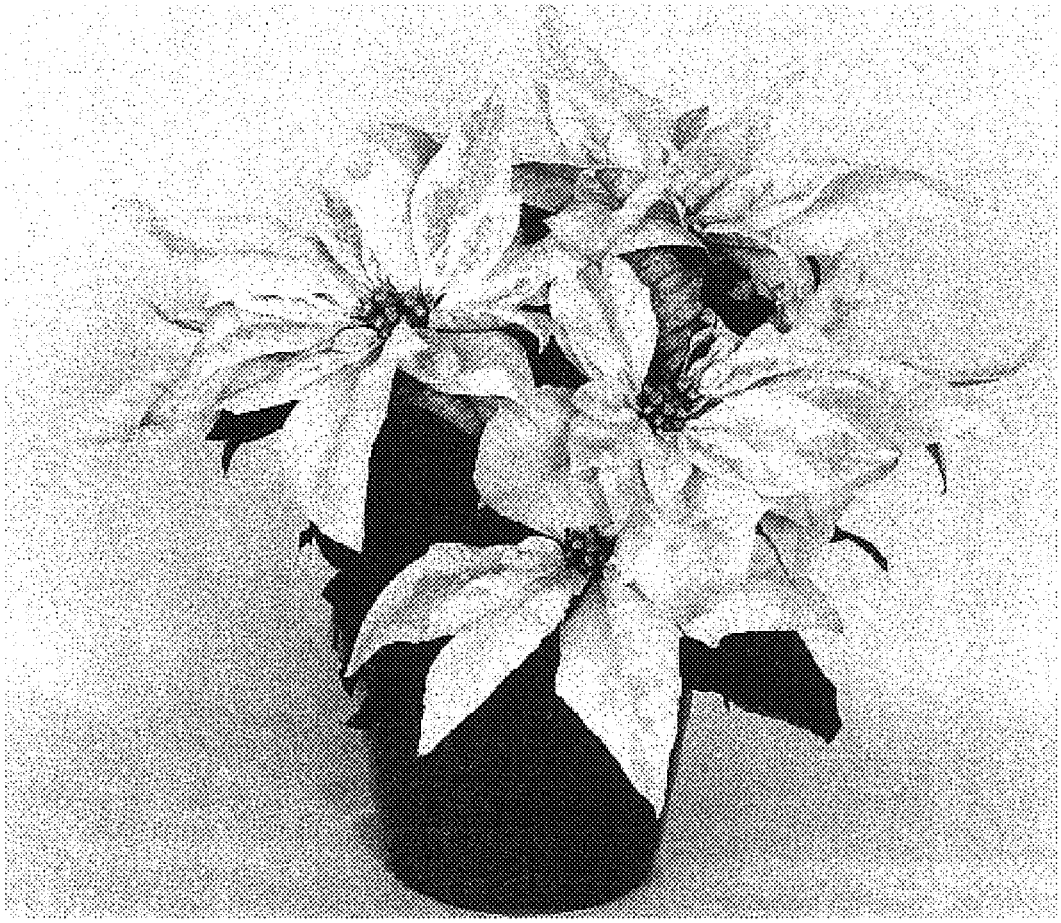
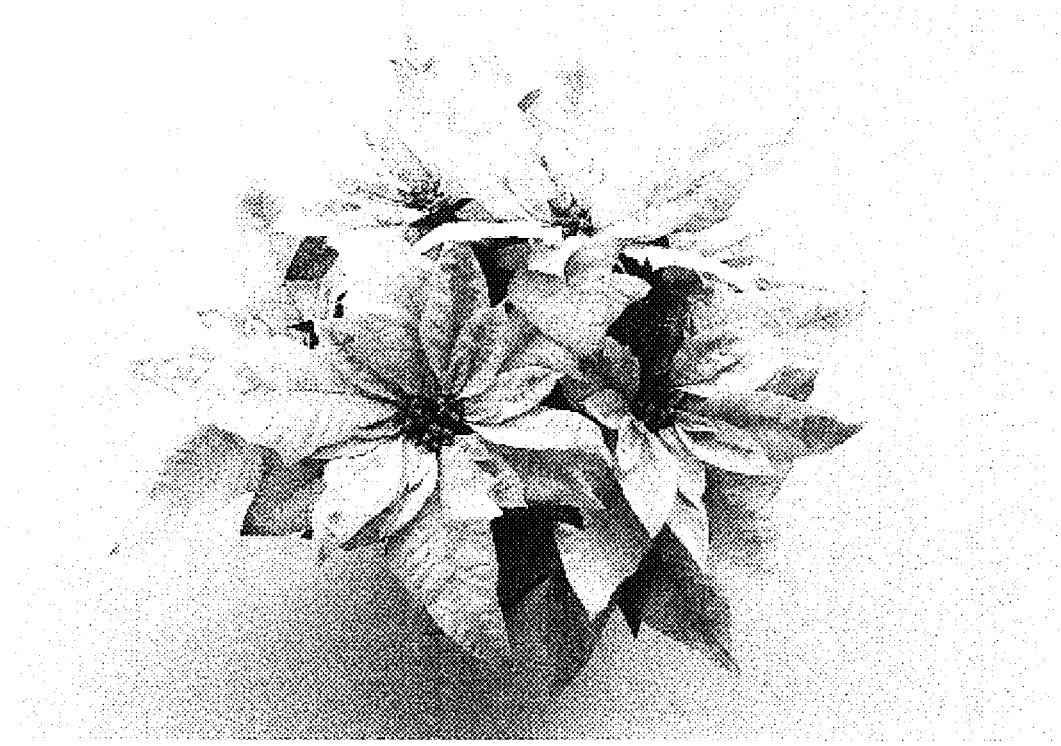

* * * * *